US006920880B1

(12) United States Patent
Zahrt et al.

(10) Patent No.: US 6,920,880 B1
(45) Date of Patent: Jul. 26, 2005

(54) MASK DEFOGGING SYSTEM AND METHOD

(76) Inventors: Justin W. Zahrt, 629 Villa Centre Way, San Jose, CA (US) 95128; William M. Hollowell, 605 Cannons Ferry Rd., Tyner, NC (US) 27980

( * ) Notice: Subject to any disclaimer, the term of this patent is extended or adjusted under 35 U.S.C. 154(b) by 0 days.

(21) Appl. No.: 10/884,909

(22) Filed: Jul. 6, 2004

(51) Int. Cl.[7] ................................................ A61B 18/08
(52) U.S. Cl. .............................. 128/206.22; 128/206.29
(58) Field of Search ............................ 128/863, 201.15, 128/201.14, 201.17, 204.25, 205.19, 206.22, 206.29

(56) References Cited

U.S. PATENT DOCUMENTS 3,438,370 A * 4/1969 Krantz, Jr. .................. 128/139
3,742,607 A * 7/1973 Johnson ........................ 433/91
4,719,911 A * 1/1988 Carrico .................. 128/206.29
4,875,235 A * 10/1989 Kuhlman ........................... 2/8
4,890,609 A * 1/1990 Wilson, II ............. 128/206.29
5,519,896 A 5/1996 Ford
5,966,746 A 10/1999 Reedy et al.
5,996,129 A 12/1999 Lopez
6,049,917 A 4/2000 Ryden
6,138,285 A 10/2000 Robrahn et al.
6,425,143 B1 * 7/2002 Benedict et al. ............... 2/424
6,450,639 B1 9/2002 Abraham
2004/0221841 A1 * 11/2004 Herschel ................ 128/201.26

* cited by examiner

*Primary Examiner*—Henry Bennett
(74) *Attorney, Agent, or Firm*—Justin W. Zahrt

(57) ABSTRACT

A method for purging air in a goggle area on the interior of a face mask is provided. A mouthpiece is positioned in front of a mouth of a person. Positive purging of air in the goggle area on the interior of the face mask is assured by permitting air to flow from the goggle area on the interior of the face mask to the mouthpiece airway while substantially preventing air flow in the opposite direction to the goggle area. Air is purged through the mouthpiece by affirmative, breath-driven, passive ventilation while permitting a person to breathe freely and without distraction, obstruction, or deliberate action, by normal breathing with the lips in a natural position just behind the mouthpiece. Increased ventilation on the interior of the face mask is selectively forced by puckering the person's lips to engage the mouthpiece while not requiring support or retention of the mouthpiece.

20 Claims, 3 Drawing Sheets

MASK DEFOGGING SYSTEM AND METHOD

BACKGROUND

1. Technical Field

The present invention relates to ventilation systems for masks, and more particularly to new and improved active/passive ventilation systems and methods for the goggles of a face mask.

2. Background Art

Fog formation on the eye-protecting goggles of face masks has long been a problem. The major difficulty is the limited ventilation in the small space that protects and surrounds the eye area of the wearer. Solutions typically fall into three areas: improving ventilation, heating the transparent screen (window), or coating the screen with water-repellant materials. Some of these solutions have been "passive", in the sense that they try to prevent fogging of the goggles without requiring external power or affirmative action by the wearer. Some have been "active", in the sense that they require the wearer to do something to remove or prevent fogging. Some have been "powered", in the sense that they require external power sources, such as batteries, to function.

Unfortunately, there is still a need to improve such mask defogging designs. For example, powered systems can be uncomfortably heavy. Power sources must be maintained and replenished. In addition, powered systems can be loud, preventing good hearing.

Where vigorous activities are involved, such as heavy labor or competitive sports, passive ventilation systems and anti-fog coatings can be overwhelmed by increased breathing rates, body heat, and perspiration. Furthermore, anti-fog coatings can degrade, especially after repeated washing and cleaning. Increased respiration in such cases is also incompatible with "active" ventilation systems since defogging the mask requires action by the wearer. Such action distracts or impedes the wearer at the very times that the mask should be truly free breathing (i.e., having no impediments that restrict or interfere with the wearer's breathing).

What is needed is a highly effective defogging system that operates totally passively. For competitive sports, it is particularly important that defogging the mask operates totally passively so as not to distract the wearer or interfere with speech in any way. During activities such as skiing and laboratory research, the wearer must also not be distracted with fogged masks.

What is also needed is a way to positively purge the goggle area, with no reverse air flow back into the goggle area. This is important during heavy respiration, so that portions of the wearer's humid breath are not reintroduced into the goggle area.

Furthermore, what is needed is a way for the wearer to deliberately increase ventilation in the goggle area. It must be recognized that a passive system, no matter how effective, may be used under such extreme circumstances that additional assistance from the wearer could be needed. The wearer should be able to defog the mask by deliberately forcing increased ventilation into the mask goggle area when desired.

Finally, what is needed is a way to retrofit masks that have already been fabricated with an improved defogging system. Many people, such as paintball players and motorcycle riders, have already invested in very expensive masks and helmets. Retrofitting their current masks would be highly favorable to purchasing entire new systems.

Solutions to these problems have been long sought but prior developments have not taught or suggested any solutions and, thus, solutions to these problems have long eluded those skilled in the art.

DISCLOSURE OF THE INVENTION

The present invention provides a method for purging air in the goggle area on the interior of a face mask. A mouthpiece is positioned in a service position immediately in front of the mouth of a person wearing such a face mask such that the person can selectively engage an airway in the mouthpiece by puckering the person's lips thereagainst. Positive purging of air in the goggle area on the interior of the face mask is assured by permitting air to flow from the goggle area on the interior of the face mask to the mouthpiece airway while substantially preventing air flow in the opposite direction. Air from the goggle area on the interior of the face mask is purged through the mouthpiece by affirmative, breath-driven, passive ventilation while permitting a person wearing the face mask to breathe freely and without distraction, obstruction, or deliberate action, by normal breathing with the lips in a natural position just behind the mouthpiece. Increased ventilation for the goggle area on the interior of the face mask is selectively forced by puckering the person's lips to engage the mouthpiece while not requiring support or retention of the mouthpiece manually or with the lips or teeth.

Certain embodiments of the invention have other advantages in addition to or in place of those mentioned above. The advantages will become apparent to those skilled in the art from a reading of the following detailed description when taken with reference to the accompanying drawings.

DETAILED DESCRIPTION OF THE INVENTION

In the following description, numerous specific details are given to provide a thorough understanding of the invention. However, it will be apparent that the invention may be practiced without these specific details. Likewise, the drawings showing embodiments of the device are semi-diagrammatic and not to scale and, particularly, some of the dimensions are for the clarity of presentation and are shown exaggerated in the FIGs.

Figure 1:
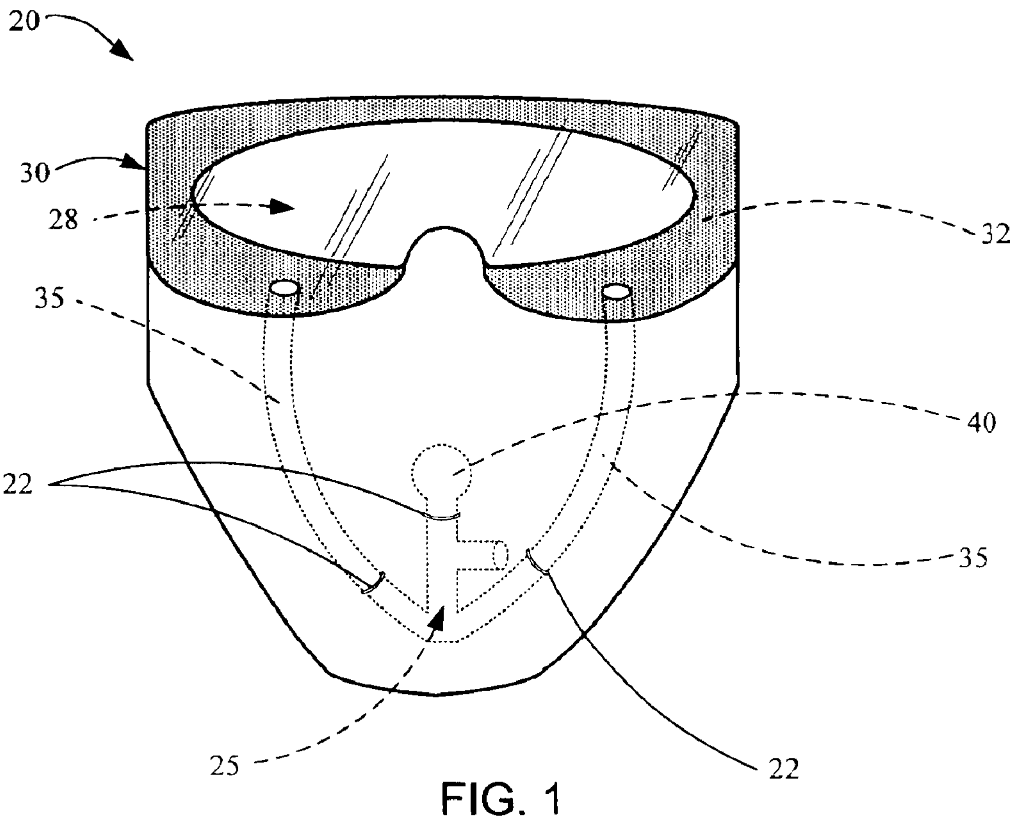
FIG. 1 is a somewhat figurative front view illustration of a face mask fitted with a mask defogging system and method according to the present invention.

With reference to the drawings, the new and improved mask defogging system and method according to the present invention will now be described. FIG. 1 shows a face mask 20 having mounting straps 22 supporting a mask defogging system 25 on the inside thereof. The mask defogging system 25 removes fog (moisture or condensate) from an interior mask goggle area 28 on the interior of the mask behind a mask screen or window, such as a window 30.

Build-up of moisture and humidity in the interior mask goggle area 28 is a common problem with protective masks that fit closely to the face for increased eye protection. A conventional mask may include, for example, a resilient goggle rim 32 that rests and largely seals against the wearer's face, encircling and protecting the wearer's eyes behind the window 30. Small ventilation openings (e.g., fine mesh ventilation grills 33, FIG. 2), most of which are not shown, are usually provided to allow for circulation, but for reasons previously discussed and all too well known, intense activities and/or warm and humid environments can render such ventilation openings inadequate.

To increase removal of such "stale" air from the interior mask goggle area 28, the mask defogging system 25 affords both passive and active enhanced defogging. The mask defogging system 25 thus includes a pair of ventilation tubes that form air flow channels 35 connected one each to each side (left and right) of the interior mask goggle area 28, such as at the fine mesh ventilation grills 33. The air flow channels 35, which draw and purge the air from the interior mask goggle area 28, are then coupled to an air flow channel 37 at the base of the face mask 20. The air flow channel 37, in turn, rises to a position in front of a mouth 39 (FIG. 3) of a person wearing the mask, and ends by coupling into a mouthpiece 40.

Figure 2:
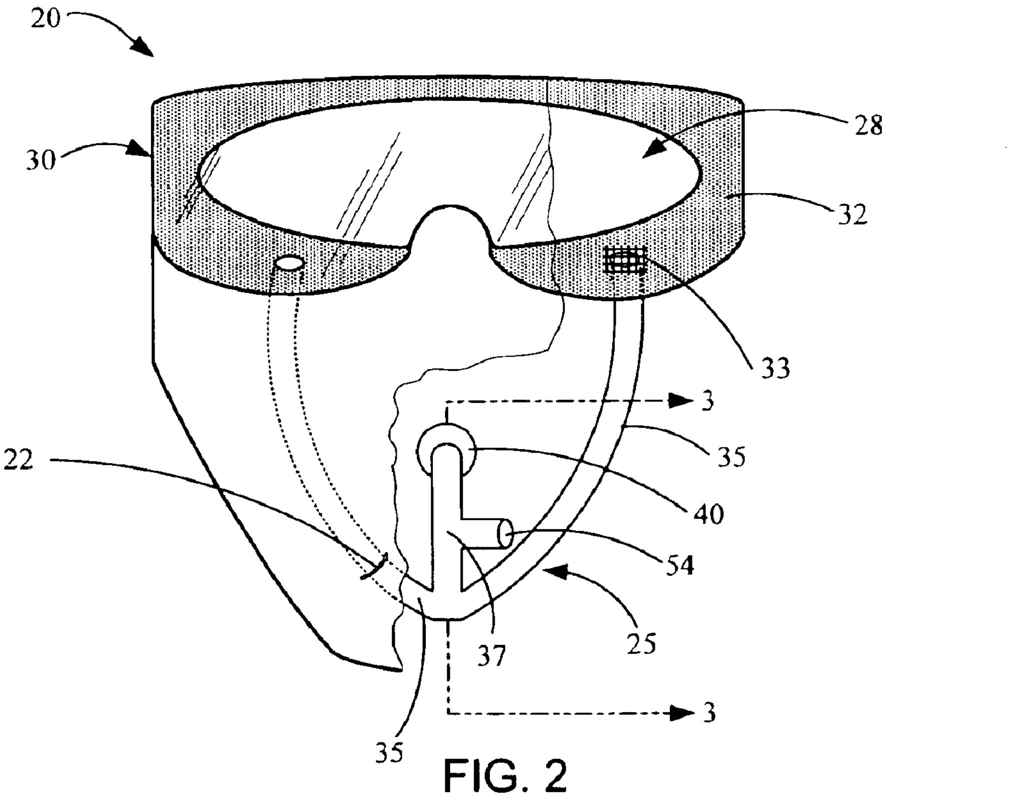
FIG. 2 is a partially broken away front view of the mask and defogging system shown in FIG. 1.

The mouthpiece 40 is supported in a service position 42 (FIG. 3) immediately in front of the mouth 39 of the person wearing the face mask 20 (FIG. 2). Thus, the person can selectively engage the mouthpiece 40 by puckering 56 the person's lips against the mouthpiece 40.

Figure 3:
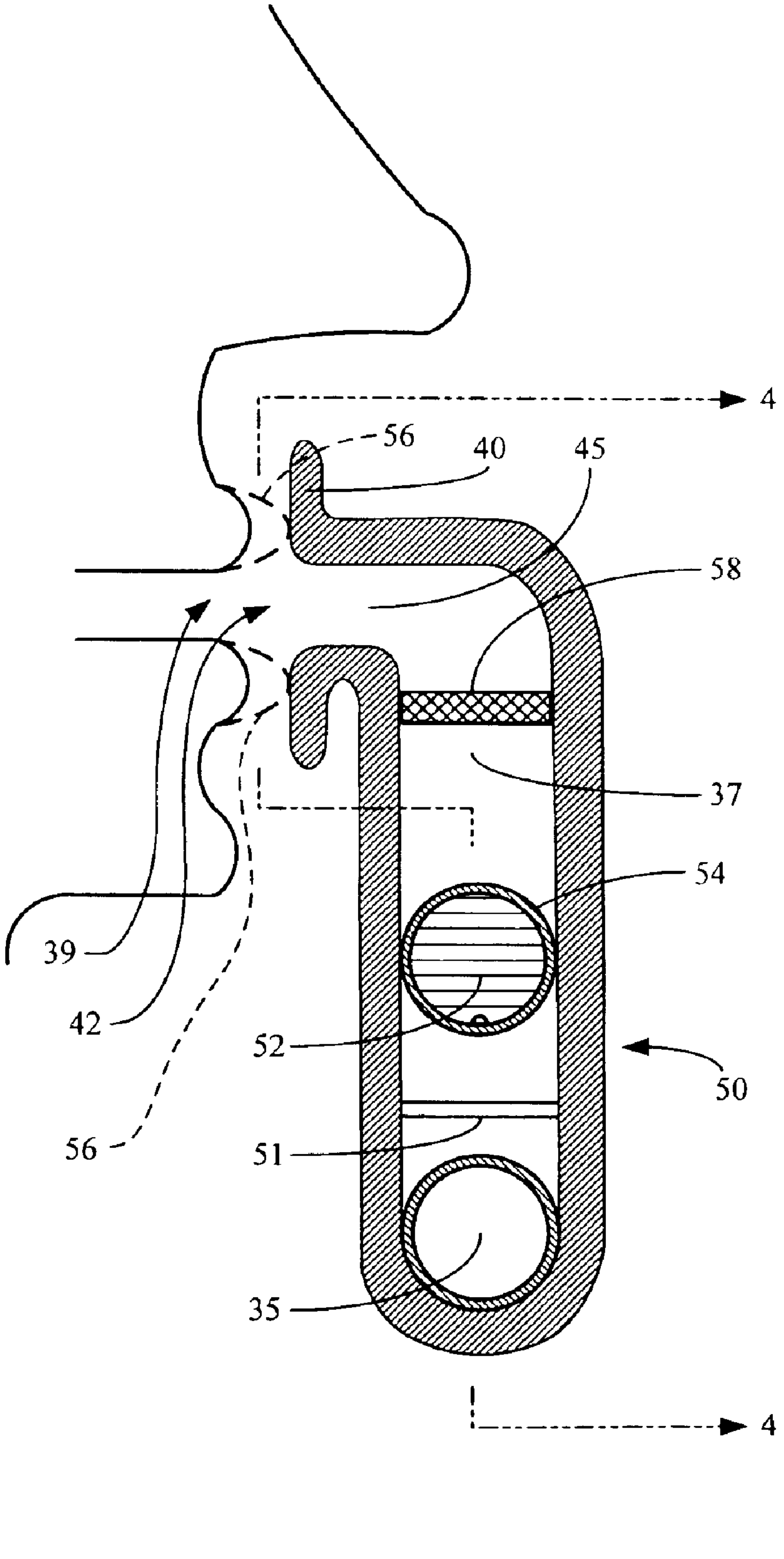
FIG. 3 is a partial cross-sectional view taken generally on line 3—3 in FIG. 2, and also showing figuratively the preferred positioning of the defogging system relative to the mouth of a wearer.

An airway 45 passing through the mouthpiece 40, to become part of the air flow channel 37, is subjected to the wearer's breath whether the wearer's lips are touching the mouthpiece 40 or not. When relaxed, the lips are in a natural position just behind the mouthpiece (as illustrated in FIG. 3), where the airway 45 is close enough to be subjected the pressure differentials as the wearer breathes. Thus, the wearer's natural inhalation and exhalation induce respective air flows in the airway 45.

Alternatively, when the wearer's lips are extended, or puckered 56, against the mouthpiece 40, the airway 45 is directly engaged. The wearer can, by thus selectively choosing to contact the mouthpiece, force increased ventilation for the interior mask goggle area 28. In either case, no effort is required by the wearer to support or retain the mouthpiece, whether manually or with the lips or teeth.

To assure positive purging of air from the mask goggle area, the present invention includes an air flow controller. In one embodiment, a two-stage air valve 50 is located in the air flow channels 35, the air flow channel 37, and the airway 45. The two-stage air valve 50 comprises an intake valve 51 and an exhaust valve 52, both shown located in the air flow channel 37. Based upon the teachings herein, it will be clear that other locations and arrangements may be selected according to design preferences and/or particular mask configurations.

Figure 4:
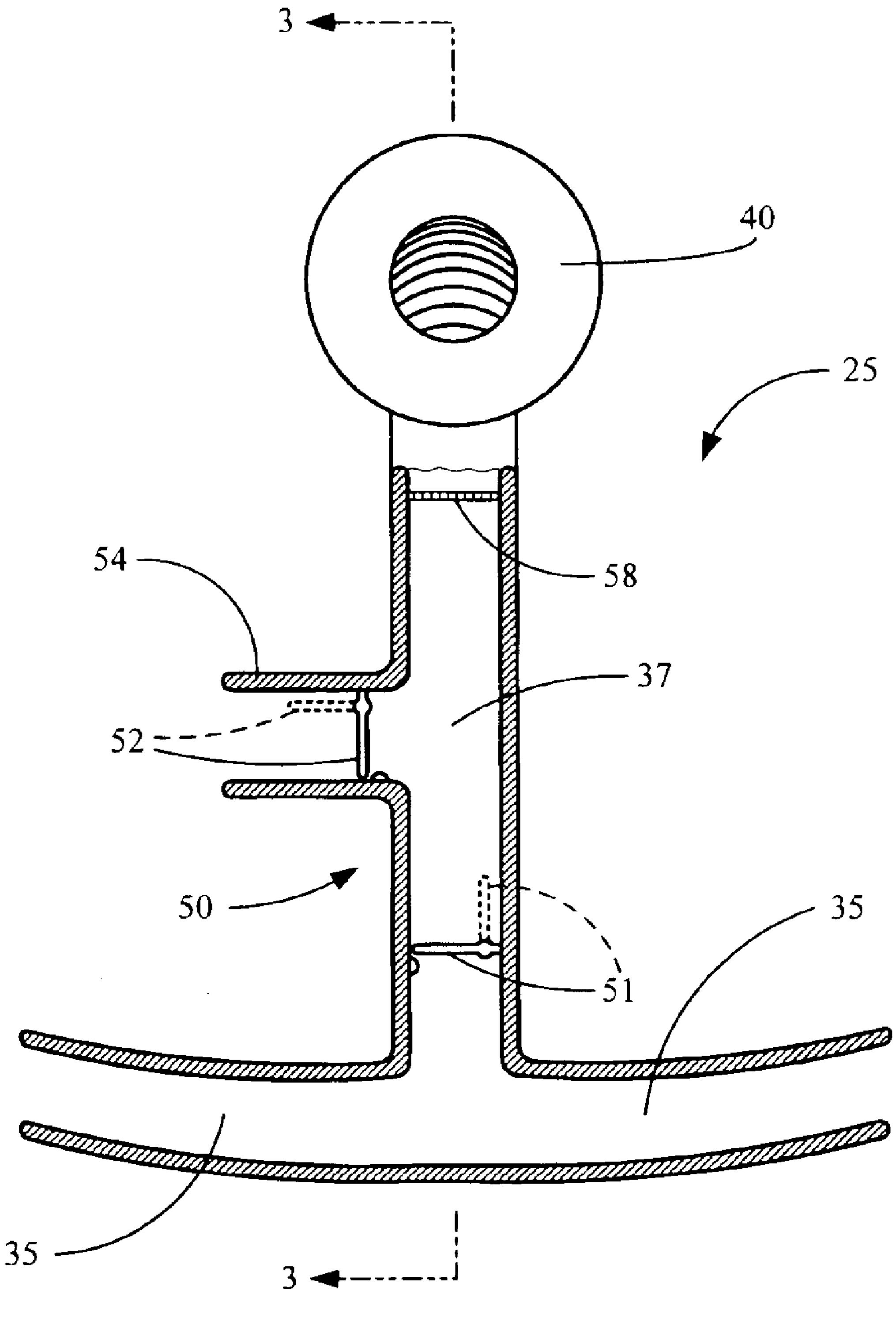
FIG. 4 is a partially broken away elevation of the defogging system taken on view line 4—4 of FIG. 3.

The intake valve 51 and the exhaust valve 52 are simple check valves such as commonly available in manual siphon pumps from Aubuchon Hardware (www.doitbest.com), located at 66 High Street, West Carthage, N.Y. 13619, and sold under the designation DH-10 PUMP, MANUAL SYPHON SKU: 405019. They are lightweight plastic flap valves that actuate easily under almost no pressure differential. When open (phantom lines in FIG. 4), the valves afford no perceptible air flow restriction to the wearer.

The intake valve 51 assures positive purging of air in the interior mask goggle area 28 on the interior of the face mask 20. As the wearer inhales, air is permitted to flow in one direction through the air flow channels 35 and 37 to the airway 45 from the interior mask goggle area 28. The intake valve 51 substantially prevents air flow in the opposite direction.

The exhaust valve 52 is connected to the air flow channel, in this case to the air flow channel 37. As the wearer exhales, the exhaust valve 52 then causes the air to flow unidirectionally from the airway 45 to an exhaust port 54. The exhaust port 54 is located to exhaust breath entering the mouthpiece 40 to a location away from the interior mask goggle area 28.

A debris filter 58, such as a fine screen, may be located in or appropriately associated with the air flow channel. The debris filter 58 captures debris in order to protect the wearer from inhaling such debris.

As may be seen, therefore, the present invention provides numerous advantages. One such advantage, which results from the location of the mouthpiece in the service position close to the wearer's mouth, is increased drawing of air through the airway 45 during passive ventilation inhalation defogging (wearer's lips relaxed) by a venturi effect at the mouthpiece 40. That is, the rapid velocity of the air in the narrow space between the mouthpiece and the wearer's lips, during inhalation, will induce an additional venturi pressure reduction in the mouthpiece airway 45, helping to draw additional air from the interior mask goggle area 28.

Another advantage during passive defogging is the wearer's ability to talk freely and without interference while still enjoying and benefiting from the mask defogging action of the present invention.

The present invention can be incorporated into face masks during their manufacture. However, another important advantage is that it can be readily retrofitted onto masks that have previously been fabricated, as by fasteners such as the mounting straps 22.

Principally, therefore, the present invention provides an economical, lightweight, convenient, uncomplicated, durable, versatile, reliable, and highly effective mask defogging system for purging air in the goggle area on the interior of a face mask. The mask defogging system and method are truly free breathing, causing no objectionable interference with the wearer's natural breathing. Positive purging assures that the wearer's humid breath will not be reintroduced into the goggle area. Passive operation assures that the defogging system and method will not distract the wearer in any way. Optional active operation assures that the wearer can always obtain the purging needed, even under highly demanding uses.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hither-to-fore set forth or shown in the accompanying drawings are to be interpreted in an illustrative and non-limiting sense.

What is claimed is:

1. A mask defogging system for purging air in the goggle area on the interior of a face mask, comprising:

a mouthpiece having an airway therethrough, a mount adapted for supporting the mouthpiece in a service position immediately in front of the mouth of a person wearing the face mask such that the person can selectively engage the mouthpiece airway by puckering the person's lips thereagainst while not requiring support or retention of the mouthpiece manually or with the lips or teeth, an air flow channel which includes the airway in the mouthpiece, and which is connected to the goggle area on the interior of the face mask to provide for purging air therefrom, and an air flow control associated with the air flow channel to assure positive purging of air in the goggle area on the interior of the face mask by permitting air to flow through the air flow channel to the mouthpiece airway from the goggle area on the interior of the face mask while substantially preventing air flow in the opposite direction to the goggle area, to provide affirmative, breath-driven, passive ventilation for the goggle area on the interior of the face mask while permitting a person wearing the mask to breathe freely and without distraction, obstruction, or deliberate action, by normal breathing with the lips in a natural position just behind the mouthpiece, and to permit the person selectively to force increased ventilation for the goggle area by puckering the person's lips to engage the mouthpiece.

2. The mask defogging system of claim 1 wherein the service position is predetermined such that the velocity of the air in the space between the mouthpiece and the wearer's lips, during passive ventilation inhalation, induces a venturi pressure reduction in the mouthpiece airway, to help draw air from the goggle area.

3. The mask defogging system of claim 1 wherein the mount further comprises a mount adapted for attaching the mouthpiece to the face mask in the service position.

4. The mask defogging system of claim 1 wherein the air flow control further comprises an air valve located therein.

5. The mask defogging system of claim 1 further comprising an exhaust port operatively connected to the air flow channel and located to exhaust breath entering the mouthpiece airway to a location away from the goggle area.

6. The mask defogging system of claim 5 wherein the air flow control further comprises a two-stage air valve located therein and connected to cause one stage thereof to cause the air to flow uni-directionally from the goggle area to the mouthpiece airway, and to cause the other stage thereof to cause the air to flow uni-directionally from the mouthpiece airway to the exhaust port.

7. The mask defogging system of claim 1 further comprising a debris filter operatively associated with the air flow channel to capture debris so as to protect the person wearing the face mask from inhaling such debris.

8. The mask defogging system of claim 1 further comprising means for retrofitting the mask defogging system onto a mask which has previously been fabricated.

9. A mask defogging system for purging air in the goggle area on the interior of a face mask, comprising:

a mouthpiece having an airway therethrough, a mount adapted for attaching the mouthpiece to such a face mask in a position immediately in front of the mouth of a person wearing the face mask such that the person can selectively engage the mouthpiece airway by puckering the person's lips thereagainst while not requiring support or retention of the mouthpiece manually or with the lips or teeth, air flow channel which includes the airway in the mouthpiece, and which is connected to the goggle area on the interior of the face mask to provide for purging air therefrom, an exhaust port operatively connected to the air flow channel and located to exhaust breath entering the mouthpiece airway to a location outside and away from the goggle area and away from the mouth of the person wearing the mask, a debris filter operatively associated with the air flow channel to capture debris so as to protect the person wearing the face mask from inhaling such debris, and air flow control associated with the air flow channel, and including a two-stage air valve located therein and connected to cause one stage thereof to cause the air to flow uni-directionally from the goggle area to the mouthpiece airway, and to cause the other stage thereof to cause the air to flow uni-directionally from the mouthpiece airway to the exhaust port, to assure positive purging of air in the goggle area on the interior of the face mask by permitting air to flow through the air flow channel to the mouthpiece airway from the goggle area on the interior of the face mask while substantially preventing air flow in the opposite direction to the goggle area, to provide affirmative, breath-driven, passive ventilation for the goggle area on the interior of the face mask while permitting a person wearing the face mask to breathe freely and without distraction, obstruction, or deliberate action, by normal breathing with the lips in a natural position just behind the mouthpiece, the service position being predetermined such that the velocity of the air in the space between the mouthpiece and the wearer's lips, during passive ventilation inhalation, induces a venturi pressure reduction in the mouthpiece airway, to help draw air from the goggle area, and to permit the person selectively to force increased ventilation for the goggle area by puckering the person's lips to engage the mouthpiece.

10. The mask defogging system of claim 9 further comprising means for retrofitting the mask defogging system onto a mask which has previously been fabricated.

11. A method for purging air in the goggle area on the interior of a face mask, comprising:

positioning a mouthpiece in a service position immediately in front of the mouth of a person wearing such a face mask such that the person can selectively engage an airway in the mouthpiece by puckering the person's lips thereagainst while not requiring support or retention of the mouthpiece manually or with the lips or teeth, assuring positive purging of air in the goggle area on the interior of the face mask by permitting air to flow from the goggle area on the interior of the face mask to the mouthpiece airway while substantially preventing air flow in the opposite direction to the goggle area, purging air from the goggle area on the interior of the face mask through the mouthpiece by affirmative, breath-driven, passive ventilation while permitting a person wearing the face mask to breathe freely and without distraction, obstruction, or deliberate action, by normal breathing with the lips in a natural position just behind the mouthpiece, and selectively forcing increased ventilation for the goggle area on the interior of the face mask by puckering the person's lips to engage the mouthpiece.

12. The method of claim 11 further comprising, by changing the velocity of the air in the space between the mouthpiece and the wearer's lips during passive ventilation inhalation, inducing a venturi pressure reduction in the mouthpiece airway, to help draw air from the goggle area.

13. The method of claim 11 further comprising attaching the mouthpiece to the face mask in the service position.

14. The method of claim 11 wherein the step of assuring positive purging further comprises permitting the air flow from the goggle area and preventing the opposite air flow at least in part by an air valve operatively located in the air flow between the goggle area and the mouthpiece.

15. The method of claim 11 further comprising exhausting breath entering the mouthpiece airway through an exhaust port located away from the goggle area.

16. The method of claim 15 wherein the step of assuring positive purging further comprises permitting the air flow from the goggle area and preventing the opposite air flow at least in part by a two-stage air valve operatively located in the air flow between the goggle area and the exhaust port and connected to cause one stage thereof to cause the air to flow uni-directionally from the goggle area to the mouthpiece airway, and to cause the other stage thereof to cause the air to flow uni-directionally from the mouthpiece airway to the exhaust port.

17. The method of claim 11 further comprising capturing debris to protect the person wearing the face mask from inhaling such debris.

18. The method of claim 11 further comprising retrofitting the mask defogging system onto a mask which has previously been fabricated.

19. A method for purging air in the goggle area on the interior of a face mask, comprising:

attaching a mouthpiece to the face mask in a service position immediately in front of the mouth of a person wearing such a face mask such that the person can selectively engage an airway in the mouthpiece by puckering the person's lips thereagainst while not requring support or retention of the mouthpiece manually or with the lips or teeth, at least in part by an intake air valve operatively located in the air flow between the goggle area and the mouthpiece, assuring positive purging of air in the goggle area on the interior of the face mask by permitting air to flow from the goggle area on the interior of the face mask to the mouthpiece airway while substantially preventing air flow in the opposite direction to the goggle area, purging air from the goggle area on the interior of the face mask through the mouthpiece by affirmative, breath-driven, passive ventilation while permitting a person wearing the face mask to breathe freely and without distraction, obstruction, or deliberate action, by normal breathing with the lips in a natural position just behind the mouthpiece, by changing the velocity of the air in the space between the mouthpiece and the wearer's lips during passive ventilation inhalation, inducing a venturi pressure reduction in the mouthpiece airway, to help draw air from the goggle area, selectively forcing increased ventilation for the goggle area on the interior of the face mask by puckering the person's lips to engage the mouthpiece, at least in part by an exhaust air valve operatively located in the air flow between the mouthpiece and an exhaust port located away from the goggle area, the exhaust air valve being connected to cause air to flow uni-directionally from the mouthpiece airway to the exhaust port, exhausting breath entering the mouthpiece airway through the exhaust port, and capturing debris to protect the person wearing the face mask from inhaling such debris.

20. The method of claim 19 further comprising retrofitting the mask defogging system onto a mask which has previously been fabricated.

* * * * *